United States Patent [19]

Flanagan et al.

[11] Patent Number: 5,248,764
[45] Date of Patent: Sep. 28, 1993

[54] CHELATE DERIVATIVES OF ATRIAL NATRIURETIC FACTOR (ANF)

[75] Inventors: Richard J. Flanagan, Hudson; F. Peter Charleson, Kirkland, both of Canada

[73] Assignee: Merck Frosst Canada, Inc., Kirkland, Canada

[21] Appl. No.: 842,753

[22] Filed: Feb. 27, 1992

Related U.S. Application Data

[63] Continuation of Ser. No. 782,711, Oct. 25, 1991, abandoned, which is a continuation of Ser. No. 367,169, Jun. 16, 1989, abandoned.

[51] Int. Cl.$^5$ .................................................. C07K 7/10
[52] U.S. Cl. ..................................... 530/324; 530/325; 530/326; 530/408; 530/409
[58] Field of Search ................ 530/408, 409, 324, 325, 530/326

[56] References Cited

U.S. PATENT DOCUMENTS 4,352,751  10/1982  Wieder et al. ..................... 530/409

Primary Examiner—Lester L. Lee
Attorney, Agent, or Firm—Robert J. North; Joseph F. DiPrima

[57] ABSTRACT

Derivatives of synthetic fragments of mammalian atrial natriuretic factor (ANF) in which a chelate molecule is attached to the N-terminal of the peptide are described. The chelate component allows the facile labelling of these peptides with metallic isotopes such as Tc-99m, Ga-67, In-111 and others. These radioactive chelates are useful in determining the in vivo behavior and fate of derivatives of ANF.

4 Claims, No Drawings

CHELATE DERIVATIVES OF ATRIAL NATRIURETIC FACTOR (ANF)

PRIOR APPLICATION DATA

This is a continuation of application Ser. No. 07/782,711, filed Oct. 25, 1991, now abandoned, which was a continuation of application Ser. No. 07/367,169, filed Jun. 16, 1989, now abandoned.

BACKGROUND OF THE INVENTION

It has been postulated for many years that the cardiac atria serve as sensors that are important in detecting changes in extracellular fluid volume (Gauer et al., Physiol, Rev. 43: 423, 1963). Such a receptor function for the cardiac atria is known in the case of vasopressin, the hypothalamic hormone important in regulating the osmotic concentration of the body fluids.

The postulated existance of a substance which would enhance urinary sodium excretion, and hence be involved in regulation of extracellular fluid volume, was demonstrated recently. De Bold et al., Life Sci. 28: 89, 1981, injected a partially purified extract of cardiac atria of rats into other anesthetized rats and observed a large increase in urine flow and in urinary sodium excretion. This relatively crude extract possessed the appropriate characteristics of an endogenous natriuretic substance.

In addition to its potent diuretic and natriuretic effects, properties that make the material especially appropriate to exert a major effect on body fluid volume regulation, it was also discovered that these extracts of cardiac atria have potent smooth muscle relaxant activity (Currie et al., Science 221: 71, 1983). Such action implies a potential direct role in regulating blood pressure as well as a role in regulating extracellular fluid volume.

Because of the immediately recognized importance of this discovery for understanding the regulation of body fluid volume and blood pressure and the obvious therapeutic potential of such a natural substance in the treatment of congestive heart failure and hypertension, numerous laboratories set about to isolate, characterize and chemically identify the active substance(s) in the cardiac atrial extracts. The active substance(s) in cardiac atria was called atrial natriuretic factor or ANF but has been referred to also as cardionatrin (de Bold et al., Life Sci. 33: 297–302, 1983) and atriopeptin (Currie et al., Science 111: 67, 1984). Atrial natriuretic factor was shown to be a family of peptides all of which have a common amino acid sequence but differ in length by the presence or absence of 1–8 amino acids on the amino or carboxyl termini.

Peptide chemists quickly produced completely synthetic material that mimicked the biological activity of the family of peptides that have been isolated from the cardiac atria.

The biological activity of ANF indicates utility in congestive heart failure where standard therapy utilizes potent diuretics in combination with peripheral vasodilating drugs. Atrial natriuretic factor combines both of these actions in one molecule which is produced naturally within the body. It is possible that the salt and water retention associated with congestive heart failure is a result of inadequeate production of ANF. If such is true, administration of ANF would allow for replacement of adequate quantities of the material.

A second major disease for which the biological activity of ANF indicates utility is essential hypertension. Standard therapy for hypertension utilizes diuretic and peripheral vasodilating drugs. Atrial natriuretic factor incorporates both of these characteristics. A specific use also may be found in the acute treatment of hypertensive crisis such as malignant hypertension where the powerful vasodilating effect of ANF would be paramount.

In addition to these two very broad categories of therapeutic utility, it is possible that those diseases which are characterized by decreases in renal function may benefit because of the favorable action of ANF on renal hemodynamics, especially enhancement of medullary blood flow.

U.S. Pat. No. 4,609,725 by Brady et al. teaches that synthetic fragments of ANF can be labelled at carboxyl terminus in the tyrosine residue by electrophillic labelling with iodine and that these radiolabelled derivatives are useful for studying the in vivo and in vitro metabolism of ANF.

OBJECTS OF THE INVENTION

It is the object of the present invention to provide radioactive derivatives of synthetic fragments of ANF in which the radioactive atom is attached to the N-terminus of the peptide by means of a chelate molecule.

It is another object of the present invention to provide easier access to radiolabelled forms of ANF than are presently available by means of electrophilic labelling with iodine, since chelate chemistry allows the synthesis of the radioactive form of ANF by the mere mixing of the chelated form of ANF with a radioactive metal.

A further object of the invention is to provide a compound useful for studying the metabolic and half-life of ANF in vivo and in vitro.

These and other objects of the invention will be apparent from the following description.

SUMMARY OF THE INVENTION

Radiolabelled forms of ANF may be produced by combining a synthetic derivative of mammalian atrial natriuretic factor which contains a chelate functionality at the N-terminal with a suitable metallic radioisotope such as Tc-99m, Ga-67 or In-111.

DETAILED DESCRIPTION

According to the present invention the chelate form of ANF has the following amino acid sequence:

A-Cys-Phe-Gly-Gly-Arg-X-Asp-Arg-Ile-Gly-Ala-Gln-Ser-Gly-Leu-Gly-Cys-Asn-Ser-Phe-Arg-Tyr-B;

where X is Ile or Met; and A is:

Ch—Ser—
Ch—Ser—Ser—
Ch—Arg—Ser—Ser—
Ch—Arg—Arg—Ser—Ser—
Ch—Leu—Arg—Arg—Ser—Ser—
Ch—Ser—Leu—Arg—Arg—Ser—Ser—
Ch—Arg—Ser—Leu—Arg—Arg—Ser—Ser—

Ch—Pro—Arg—Ser—Leu—Arg—Arg—Ser—Ser—
Ch—Gly—Pro—Arg—Ser—Leu—Arg—Arg—Ser—Ser—
Ch—Ala—Gly—Pro—Arg—Ser—Leu—Arg—Arg—Ser—Ser—
Ch—Leu—Ala—Gly—Pro—Arg—Ser—Leu—Arg—Arg—Ser—Ser— and B is absent or present and if present is:

Arg
Arg—Arg and where Ch is:
a chelate residue selected from the group consisting of:

a) 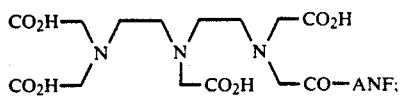

b) 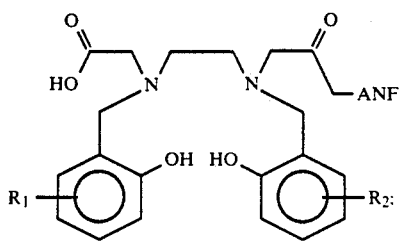

c) 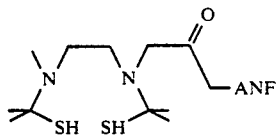

d) 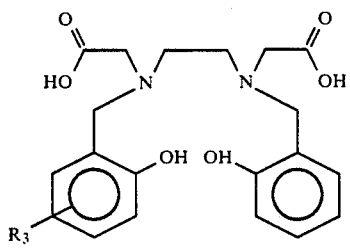

where $R_3$ = 

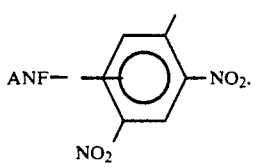

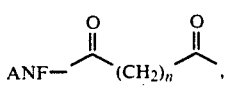

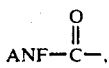

ANF—, or

and where n is 2 to 6 and the peptide is linear or cyclized by means of covalent linkages between the two cysteine residues and $R_1R_2$ which may be the same or different, is selected from hydrogen, $C_1$-$C_7$ alkyl, $C_1$-$C_7$ alkoxy, $C_3$-$C_7$ cycloalkyl, amino, halo, i.e., chloro, bromo, fluoro and iodo, trifluormethyl and the like.

Chelate a) is Diethylene-triamine-pentaacetic acid (DTPA), commercially available from Aldrich Chemical Co., Inc.; chelate b) is N,N'-di(2-hydroxybenzyl)ethylenediamine-N,N'-diacetic acid (HBED), commercially available from Strem Chemicals; and chelates c) and d) are derivatives of chelate b), using methods well known to those of ordinary skill in the art, such methods not being claimed here.

In the above where X is Ile, A is a chelate as defined such as HBED-Arg-Arg-Ser-Ser and B is absent is a preferred chelate and HBED is N,N'-bis[-2-hydroxybenzyl]ethylenediamine-N,N'-diacetic acid.

The chelated form of ANF is synthesized by first converting the ANF derivative to the tetra-hydrochloride form by passage through a suitable ion-exchange column. This is especially important if the ANF is originally in the tetraacetate form. The tetrahydrochloride form is then reacted with an active ester derivative of the chelate molecule in such a way that reaction occurs at the N-terminal of the peptide. The resulting mixture of chelated ANF, unchelated ANF and unreacted active chelate ester is then purified by preparative HPLC to obtain the pure chelated ANF derivative. This chelated ANF form is then reacted in ion-free water with a metallic radioisotope, such as $^{67}$Ga, gallium citrate, $^{111}$In, indium chloride or $^{99m}$Tc-technetium ions in the IV or V state.

In practice these modified chelate forms of ANF are dissolved in a buffer carrier, lyophillized and delivered to the end user in unit doses of 10 to 300 micrograms of ANF per vial. The user will add a solution of a metallic radioisotope to the lyophillized chelate and after a period of minutes during which the metal chelate complex forms the labelled ANF complex is ready for use.

Radioisotopes for which these chelates are suitable are $^{99m}$Technetium, $^{67}$Gallium, $^{68}$Gallium, $^{51}$Chromium, $^{57}$Cobalt, $^{60}$Cobalt, $^{111}$Indium, $^{113m}$Indium, $^{186}$Rhenium, $^{188}$Rhenium, $^{90}$Yttrium and the like.

In order to further illustrate the practice of the present invention, the following Examples are included.

EXAMPLE 1

Preparation of ANF tetra-hydrochloride

Human ANF fragment (methionine at the 10 position) was examined by 300 MHz NMR spectrometry to confirm the presence of the tetra-acetate groups. 10 milligrams of this sample was dissolved in 2 mL of ultra-pure water (resistance ≧ 18 MOhms) and passed through a small column containing 1 gram of Dowex AG3-X4 (chloride form). The eluate was recovered and the column further washed with ultrapure water. The tetrahydrochloride ANF was recovered from the eluate by lyophilization. Yield 9.6 mg. The NMR spectrum of this material confirms the absence of acetate.

EXAMPLE 2

Reaction of ANF with N,N-bis[2-(2,6-dioxomorpholino)ethyl]-glycine 1.0 mG of tetra-hydrochloride human ANF (methionine at the 10 position) was reacted in 40 microliters of 0.1M NaHCO3 buffer at pH 8.2 with a solution of N,N-bis[2-(2,6-dioxomorpholino)-ethyl]-glycine (160 micrograms, 448 nmoles, in 4 microliters of dimethyl sulphoxide (DMSO)). The mixture was allowed to stand overnight and then saturated with $CO_2$ gas. An analysis of this solution by means of radiochromatography (ITLC-silica gel/$CO_2$ saturated saline) was carried out with $^{111}$-InCl3 indicating that 82% of the radioactivity was bound to the ANF molecule.

This mixture of crude ANF derivative was purified by preparative HPLC chromatography, using a Waters C8 reverse phase column and 81:19 water/acetonitrile as solvent. The elution time of unchelated ANF using this system was 2.18 minutes and that of the chelated form was 3.28 minutes. The isolated yield of purified diethylenetriaminepentacetic acid ANF was 319 micrograms.

EXAMPLE 3

Reaction of the diethylenetriaminepentacetic acid derivative of ANF with $^{111}$In-Indium Chloride 25 microliter of ultrapure water was added to 25 microliters of $^{111}$Indium Chloride stock solution (Atomic Energy of Canada Limited). Add 100 microliters of 0.01M sodium citrate pH 5.0 buffer, followed by 10 microliters of solution containing 16 micrograms of the diethylenetriaminepent acetic acid derivative of ANF. Reaction is almost instantaneous and analysis by radiochromatography on ITLC indicated a labelling yield of 83%.

EXAMPLE 4

Preparation of N,N'-bis-[2-hydroxybenzyl] ethylenediamine-N,N'diacetic acid-N"'-Hydroxy-Succinimide Ester 106 mg of N,N'-bis[2-hydroxybenzyl]ethylenediamine-N,N'diacetic acid (HBED) was dissolved in 1 mL of acetonitrile and the solution saturated with trimethylamine gas. The insolubles were removed by filtration and the solute evaporated to dryness at 90° under high vacuum. The residue was dissolved in 5 mL of acetonitrile containing 205 mg of disuccinidmyl carbonate. After 1 hour the acetonitrile was removed under vacuum. The residue is quickly partitioned between water and chloroform and the chloroform layer is isolated, dried over sodium sulphate and removed in vacuo to give the crude ester. $^1$HMR confirms the presence of two succinidimyl residues per HBED molecule. Since this is a very reactive ester it is used without further purification.

EXAMPLE 5

Reaction of ANF with N,N'-bis-[2-hydroxybenzyl]-ethylenediamine-N,N'diacetic acid -N"-Hydroxy-Succinimide Ester 0.38 mg of the above active ester was reacted with 1 mg of human atrial natriuretic factor tetrahydrochloride in 110 microlites of dry dimethyl sulphoxide and 2.7 microliter of dry pyridine. Analysis by thin layer chromatography showed the conversion of ANF (O-phthaldehyde positive, UV negative) to a new derivative (O-phthaldehyde negative, UV positive). After 16 hours the solution was evaporated to dryness and the residue taken up in methanol and the insoluble protein fraction isolated and purified by chromatography and lyophillized in lots of 0.5 mg.

EXAMPLE 6

Labelling of the N,N'-bis-[2-hydroxybenzyl]-ethylenediamine-N,N'diacetic acid derivative of ANF with $^{111}$ Indium Chloride 2mCi of $^{111}$InCl3 in 1 mL of 0.1M sodium citrate buffer (pH 5.4) was added to a vial containing 0.5 mg of lyophillized ANF. After 5 minutes the solution was analyzed by ITLC showing a labelling yield of 90%.

What is claimed is:

1. A chelated peptide wherein said chelate is selected from the group consisting of

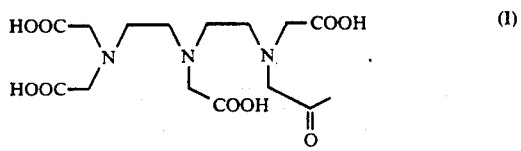
(I)

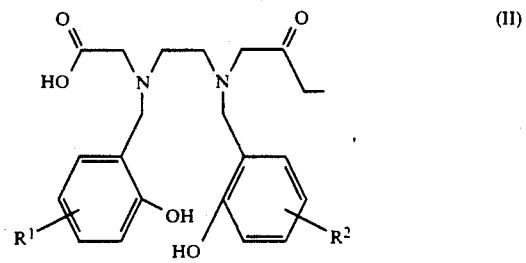
(II)

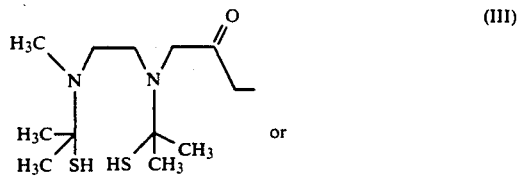
(III)

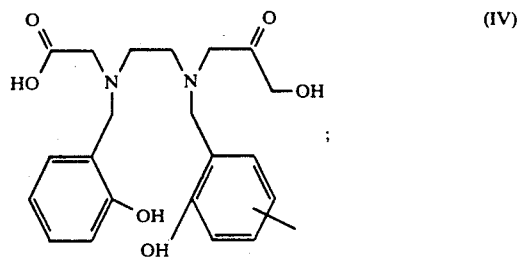
(IV)

wherein:
R$^1$ and R$^2$ are independently
C$_{1-7}$ alkyl,

C<sub>1-7</sub> alkoxy,
C<sub>3-7</sub> cycloalkyl,
halo,
amino or
trifluoromethyl;
provided that when said chelate is I, II or III then said chelate is bonded to ANF by a covalent bond and further provided that when said chelate is IV, then said chelate is either bonded to ANF by a covalent bond or is linked by an R³ group;
R³ is

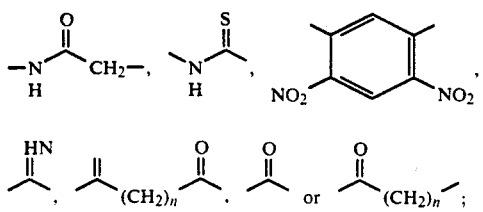

ANF is

A—Cys—Phe—Gly—Gly—Arg—X—Asp—Arg—Ile—Gly—Ala—

Gln—Ser—Gly—Leu—Gly—Cys—Asn—Ser—Phe—Arg—Tyr—B;

X is Ile or Met;
A is

—Ser—,

—Ser—Ser—,

—Arg—Ser—Ser—,

—Arg—Arg—Ser—Ser—.

—Leu—Arg—Arg—Ser—Ser—,

—Ser—Leu—Arg—Arg—Ser—Ser—,

—Arg—Ser—Leu—Arg—Arg—Ser—Ser—,

—Pro—Arg—Ser—Leu—Arg—Arg—Ser—Ser—.

—Gly—Pro—Arg—Ser—Ser—Arg—Arg—Ser—Ser—,

—Ala—Gly—Pro—Arg—Ser—Leu—Arg—Arg—Ser—Ser— or

—Leu—Ala—Gly—Pro—Arg—Ser—Leu—Arg—Arg—Ser—Ser—;

B is present or absent and when present is

—Arg or

—Arg—Arg; and n is an integer of from 2 to 6.

2. A peptide of claim 1 where X is Ile.
3. A peptide of claim 1 where X is Met.
4. A peptide of claim 1 where X is Ile, A is N,N'-bis[2-hydroxybenzyl]ethylenediamine-N,N'diacetic acid-Arg-Arg-Ser-Ser and B is absent.

* * * * *